(12) United States Patent
Hirata

(10) Patent No.: US 8,356,899 B2
(45) Date of Patent: Jan. 22, 2013

(54) SLEEPINESS SIGNAL DETECTOR

(75) Inventor: Yutaka Hirata, Aichi (JP)

(73) Assignee: Chubu University Educational Foundation, Aichi (JP)

( * ) Notice: Subject to any disclaimer, the term of this patent is extended or adjusted under 35 U.S.C. 154(b) by 130 days.

(21) Appl. No.: 13/050,811

(22) Filed: Mar. 17, 2011

(65) Prior Publication Data

US 2012/0069301 A1 Mar. 22, 2012

Related U.S. Application Data

(63) Continuation of application No. PCT/JP2009/004572, filed on Sep. 14, 2009.

(30) Foreign Application Priority Data

Sep. 18, 2008 (JP) ................................. 2008-238931

(51) Int. Cl.
*A61B 3/14* (2006.01)
(52) U.S. Cl. ....................................................... 351/209
(58) Field of Classification Search .................. 351/209; 340/576, 575, 689
See application file for complete search history.

(56) References Cited

U.S. PATENT DOCUMENTS 5,907,282 A * 5/1999 Tuorto et al. .................. 340/576

FOREIGN PATENT DOCUMENTS

| JP | 10-272960 | 10/1998 |
|---|---|---|
| JP | 2008-079737 | 4/2008 |
| WO | WO 2010-032424 | 3/2010 |

OTHER PUBLICATIONS

Yutaka Hirata et al., "Doteki Shikaki Anteika no Nonai Joho Shori", The Brain & Neural Networks, 2004, vol. 11, No. 4, 176-192.
World Intellectual Property Organization, International Search Report and Written Opinion for International Application No. PCT/JP2009/004572, mail date Nov. 2, 2009, pp. 1-6.
International Preliminary Report on Patentability for International Application No. PCT/JP2009/004572, mail date Aug. 3, 2010, pp. 1-5.

\* cited by examiner

*Primary Examiner* — Euncha Cherry
(74) *Attorney, Agent, or Firm* — SoCal IP Law Group LLP; Steven C. Sereboff; John E. Gunther

(57) ABSTRACT

A sleepiness sign detection apparatus, includes: a head movement detection unit configured to detect a head movement to generate a head movement data; an eye movement detection unit configured to detect an eye movement to generate an eye movement data; an ideal eye movement angular velocity calculation unit configured to calculate an ideal eye movement angular velocity based on the head movement data generated by the head movement detection unit; an eye-rotation angular velocity calculation unit configured to calculate an eye-rotation angular velocity based on the eye movement data generated by the eye movement detection unit; and a sleepiness sign detection unit configured to detect vestibule-ocular reflex (VOR) from the ideal eye movement angular velocity and the eye-rotation angular velocity, and determine a sign of sleepiness based on the vestibule-ocular reflex.

8 Claims, 6 Drawing Sheets

SLEEPINESS SIGNAL DETECTOR

CROSS REFERENCE TO RELATED APPLICATIONS

This is a continuation application of International Patent Application No. PCT/JP2009/004572 filed Sep. 14, 2009 claiming priority upon Japanese Patent Application No. 2008-238931 filed Sep. 18, 2008, of which full contents are incorporated herein by reference.

BACKGROUND OF THE INVENTION

1. Field of the Invention

The present invention relates to a sleepiness sign detection apparatus for detecting a sign of sleepiness of a vehicle driver and a facility operator before they become aware of sleepiness, by taking advantage of vestibule-ocular reflex induced by a head movement.

2. Description of the Related Art

The objective detection of an arousal level is effective in preventing an accident caused by the reduction in an arousal level of a vehicle driver or a machine operator, i.e. sleepiness. Conventionally, sleepiness detection apparatuses which detect sleepiness by using biological signals such as brain waves, blinking, and eye movements resulting from sleepiness as indices have been proposed as those for detecting the sleepiness of a vehicle driver. For example, Japanese Patent Application Laid-Open No. H10-272960 discloses a sleepiness detection apparatus for, based on a blink evaluation time set on the basis of a closing time at the time of a blink unique to a driver in an arousal state, detecting a blink having a closing time longer than a blink evaluation time, and detecting sleepiness based on a ratio of the number of long blinks relative to the total number of blinks for a predetermined time.

Upon objectively detecting an arousal level, it is regarded as more effective for accident prevention to catch a sign of an arousal level reduction and prevent the reduction in the arousal level by a suitable measure than to increase the once lowered arousal level. However, the above technology had a problem of being unable to detect a sign of an arousal level reduction although it can detect a lowered arousal level, i.e. sleepiness. On the other hand, an arousal level reduction detection method focused on pupil fluctuation of a vehicle driver has been proposed as a method which suggests a possibility of sleepiness sign detection. Since pupils show large low frequency fluctuation (LLFF) when a subject is aware of sleepiness and show gradual miosis (GM) before the subject becomes aware of sleepiness, it is suggested that LLFF can be an index of conscious sleepiness and GM can be an index of sleepiness sign before awareness. However, since the size of the pupils changes according to an external luminance change and a distance to a gaze point, the above detection is thought to effectively function on straight roads where there are no oncoming vehicles at night, but may not be able to detect sleepiness with high reliability in driving conditions such as day-time driving and night-time driving when there are many oncoming vehicles.

Accordingly, an object of the present invention is to realize a sleepiness sign detection apparatus with a wide operating condition range for detecting a sign of sleepiness a vehicle driver, a machine operator and the like before they become aware of sleepiness.

SUMMARY OF THE INVENTION

For the purpose of accomplishing the above object, with respect to a first aspect of the present invention, in a sleepiness sign detection apparatus, there is used technical means including: a head movement detection unit configured to detect a head movement to generate a head movement data; an eye movement detection unit configured to detect an eye movement to generate an eye movement data; an ideal eye movement angular velocity calculation unit configured to calculate an ideal eye movement angular velocity based on the head movement data generated by the head movement detection unit; an eye-rotation angular velocity calculation unit configured to calculate an eye-rotation angular velocity based on the eye movement data generated by the eye movement detection unit; and a sleepiness sign detection unit configured to detect vestibule-ocular reflex (VOR) from the ideal eye movement angular velocity and the eye-rotation angular velocity, and determine a sign of sleepiness based on the vestibule-ocular reflex.

It is regarded as important to objectively detect an arousal level to prevent an accident caused by the reduction in an arousal level of a vehicle driver or a machine operator. The applicant focused on vestibule-ocular reflex (VOR), which is a reflexive eye movement to obtain a clear vision by rotating eye balls substantially at the same velocity in an opposite direction to a head movement, as an objective index for detecting sleepiness of a person and confirmed its effectiveness by an experiment. According to the first aspect of the present invention, the head movement is detected by the head movement detection unit, the eye movement is detected by the eye movement detection unit, the ideal eye movement angular velocity is calculated by the ideal eye movement angular velocity calculation unit on the basis of the head movement data generated by the head movement detection unit, the eye-rotation angular velocity is calculated by the eye-rotation angular velocity calculation unit on the basis of the eye movement data generated by the eye movement detection unit, the vestibule-ocular reflex from the ideal eye movement angular velocity and the eye-rotation angular velocity is detected by the sleepiness sign detection unit, and thereby, a sign of sleepiness of a vehicle driver, a machine operator, and the like before they become aware of sleepiness can be determined by the sleepiness sign detection unit based on the vestibule-ocular reflex. Since the vestibule-ocular reflex is less subject to an external environment such as ambient brightness, an operating condition range can be widened. Furthermore, since an operation load is small, real-time measurement and determination are possible.

With respect to a second aspect of the present invention, in the sleepiness sign detection apparatus of the first aspect of the present invention, there is used technical means where the sleepiness sign detection unit calculates a VOR gain defined by G and a decrease rate of the VOR gain, the G obtained by approximating the eye-rotation angular velocity by a linear equation of the ideal eye movement angular velocity:

$$e(t) = G \cdot h(t-\tau) + dc + \epsilon(t),$$

where e(t) represents eye-rotation angular velocity; G represents VOR gain; h(t) represents ideal eye movement angular velocity; $\tau$ represents delay time of eye movement with respect to head movement; dc represents constant term; and $\epsilon(t)$ represents residual of regression model, and determines a sign of sleepiness, when the decrease rate of the VOR gain exceeds a threshold value set in advance.

A decrease of the VOR gain is effective as an index indicating a sign of sleepiness since it occurs before sleepiness is felt. Since the sleepiness sign detection unit determines a sign of sleepiness when the decrease rate of the VOR gain exceeds the threshold value set in advance according to the second aspect of the present invention, the decrease of the VOR gain can be suitably used for sleepiness sign determination.

With respect to a third aspect of the present invention, in the sleepiness sign detection apparatus of the first or second aspect of the present invention, there is used technical means where the sleepiness sign detection unit calculates an approximation residual defined by $\epsilon(t)$ and a residual standard deviation, the $\epsilon(t)$ obtained by approximating the eye-rotation angular velocity by a linear equation of the ideal eye movement angular velocity:

$$e(t)=G \cdot h(t-\tau)+dc+\epsilon(t),$$

where e(t) represents eye-rotation angular velocity; G represents VOR gain; h(t) represents ideal eye movement angular velocity; $\tau$ represents delay time of eye movement with respect to head movement; dc represents constant term; and $\epsilon(t)$ represents residual of regression model, and determines a sign of sleepiness, when an increase rate of the residual standard deviation exceeds a threshold value set in advance.

An increase of the residual standard deviation is effective as an index indicating a sign of sleepiness since it occurs before sleepiness is felt. Since the sleepiness sign detection unit determines a sign of sleepiness when the increase rate of the residual standard deviation exceeds the threshold value set in advance according to the third aspect of the invention, the increase of the residual standard deviation can be suitably used for sleepiness sign determination. Particularly, when being used together with the detection apparatus according to the second aspect of the present invention, accuracy of sleepiness sign determination can be improved.

With respect to a fourth aspect of the present invention, in the sleepiness sign detection apparatus of any one of the first to third aspects of the present invention, there is used technical means where the sleepiness sign detection apparatus is a sleepiness detection apparatus installed in a vehicle, and the ideal eye movement angular velocity is calculated on the basis of outputs of an acceleration sensor and a gyro sensor provided in the vehicle as the head movement detection unit.

In the case of using the sleepiness sign detection apparatus in the vehicle according to the fourth aspect of the present invention, the outputs of the acceleration sensor and the gyro sensor provided in the vehicle as the head movement detection unit can be used to calculate the ideal eye movement angular velocity. Thus, the number of constituent members of the sleepiness sign detection apparatus can be reduced.

BRIEF DESCRIPTION OF THE DRAWINGS

For more thorough understanding of the present invention and advantages thereof, the following description should be read in conjunction with the accompanying drawings, in which.

DETAILED DESCRIPTION OF THE PREFERRED EMBODIMENTS

At least the following details will become apparent from descriptions of this specification and of the accompanying drawings.

Figure 1:
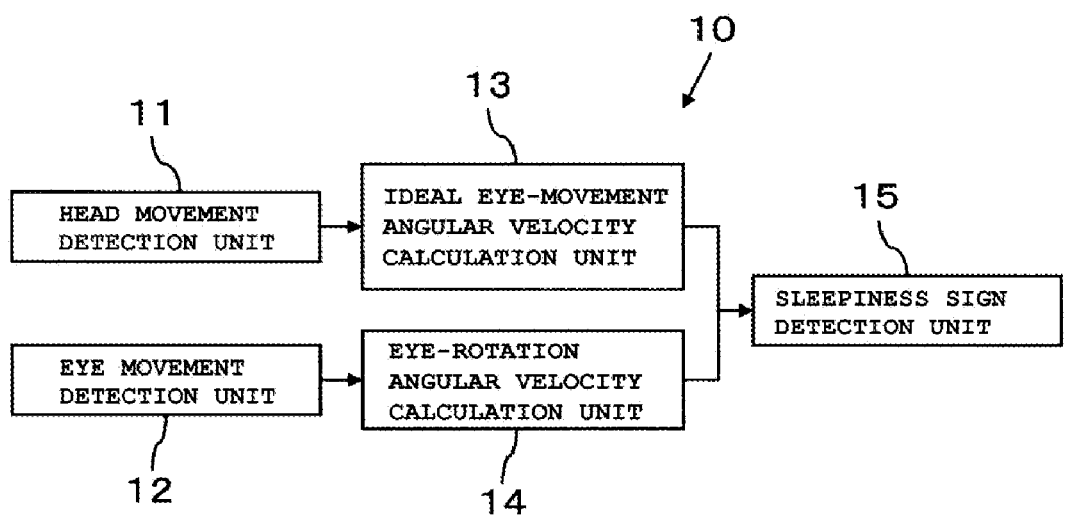
FIG. 1 is a construction diagram of a sleepiness sign detection apparatus.
Figure 2:
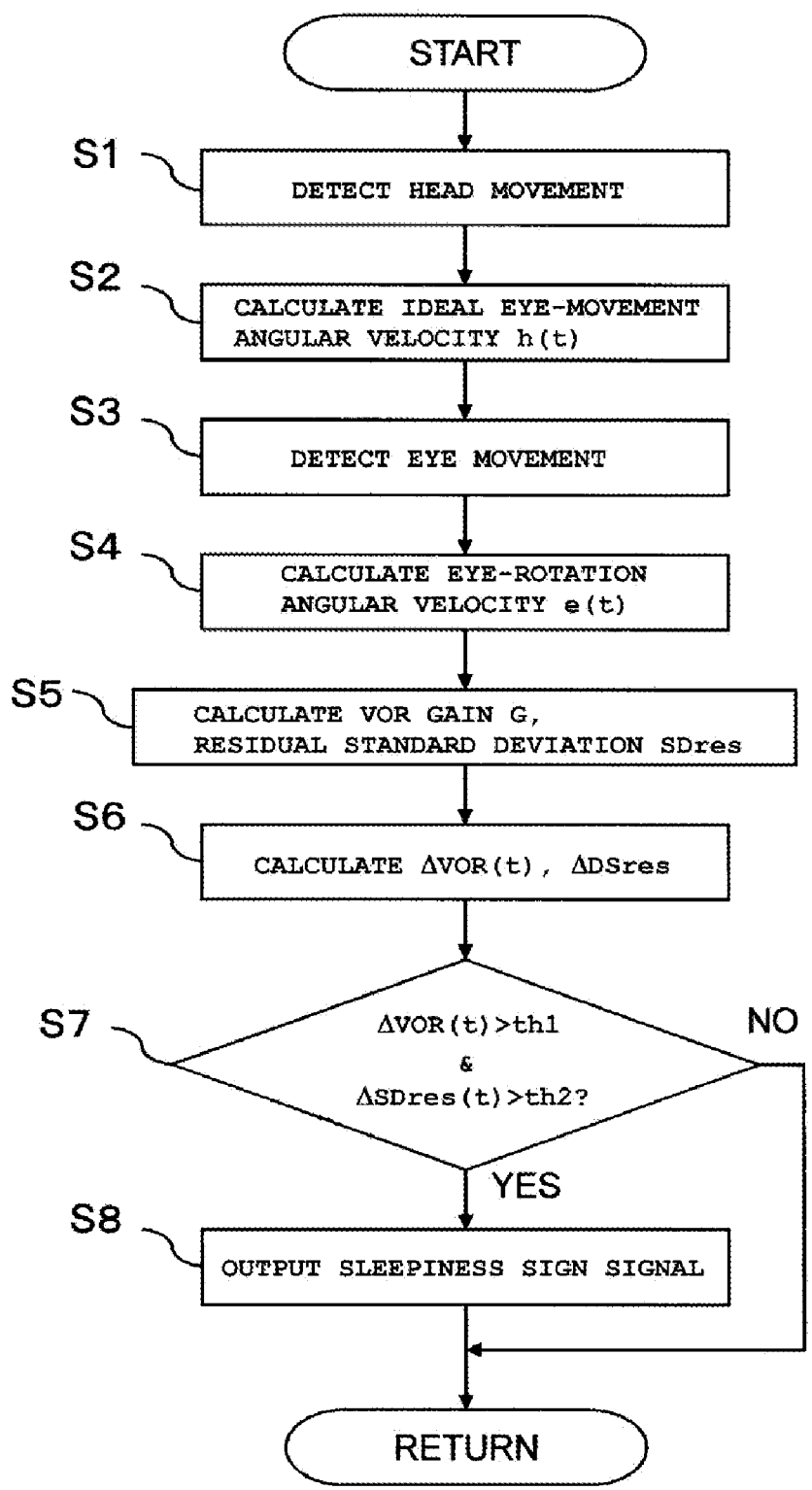
FIG. 2 is a flow diagram showing a sleepiness sign detection method.

A sleepiness sign detection apparatus according to the present invention is described with reference to the drawings. FIG. 1 is a construction diagram of the sleepiness sign detection apparatus. FIG. 2 is a flow diagram showing a sleepiness sign detection method.

As shown in FIG. 1, the sleepiness sign detection apparatus 10 includes a head movement detection unit 11 configured to detect a head movement, an eye movement detection unit 12 configured to detect an eye movement, an ideal eye movement angular velocity calculation unit 13 configured to calculate an ideal eye movement angular velocity based on head movement data detected by the head movement detection unit 11, an eye-rotation angular velocity calculation unit 14 configured to calculate an eye-rotation angular velocity based on eye movement data detected by the eye movement detection unit 12, and a sleepiness sign determination unit 15 configured to detect vestibule-ocular reflex (VOR) based on the ideal eye movement angular velocity and the eye-rotation angular velocity and determine a sign of sleepiness based on this vestibule-ocular reflex.

The head movement detection unit 11 is configured to detect linear accelerations and rotation angular velocities produced in a head. A three-axis acceleration sensor for detecting linear accelerations and a gyroscope for detecting rotation angular velocities can be used as such. For example, in the case of installation in a vehicle such as an automobile, the head movement detection unit 11 is so constructed as to be able to detect linear accelerations in a traveling direction, a vertical direction, and a lateral direction of a driver and rotation angular velocities in a rolling direction, a pitching direction, a yawing direction of the driver. Thus, head movements are respectively detected and acceleration data and rotation angular velocity data are sent to the ideal eye movement angular velocity calculation unit 13.

The eye movement detection unit 12 is configured to take an eye image. For example, a digital photographing apparatus such as a CCD camera can be suitably used as such. In the case of installing the sleepiness sign detection apparatus 10, for example, in a vehicle such as an automobile, it can be arranged at a position where an image of driver's eye balls can be easily taken such as near an instrumental panel.

The ideal eye movement angular velocity calculation unit 13 is connected to the head movement detection unit 11, and is configured to calculate an ideal eye movement angular velocity, which is an angular velocity of an ideal eye movement for compensating for a head movement, based on the head movement data detected by the head movement detection unit 11. A processing personal computer (PC) may be, for example, used as the ideal eye movement angular velocity calculation unit 13.

The eye-rotation angular velocity calculation unit 14 is connected to the eye movement detection unit 12, and is configured to calculate an eye-rotation angular velocity based on the eye movement data detected by the eye movement detection unit 12. Similar to the ideal eye movement angular velocity calculation unit 13, a processing personal computer (PC) may be, for example, used as the eye-rotation angular velocity calculation unit 14.

The sleepiness sign detection unit 15 is connected to the ideal eye movement angular velocity calculation unit 13 and the eye-rotation angular velocity calculation unit 14, and is configured to calculate a VOR gain G and a residual standard deviation to be described later as parameters on the vestibule-ocular reflex (VOR) based on the ideal eye movement angular velocity and the eye-rotation angular velocity, and determine a sign of sleepiness based on at least one of the parameters. Similar to the ideal eye movement angular velocity calculation unit 13 and the eye-rotation angular velocity calculation unit 14, a processing personal computer (PC) may be, for example, used as the sleepiness sign detection unit 15.

The ideal eye movement angular velocity calculation unit 13, the eye-rotation angular velocity calculation unit 14, and the sleepiness sign detection unit 15 may be constructed by the same processing personal computer. Further, an engine control unit (ECU) may be commonly used as a processing personal computer in the case of installing the sleepiness sign detection apparatus 10, for example, in a vehicle such as an automobile. In this way, constituent members of the sleepiness sign detection apparatus 10 can be reduced in number.

Next, the sleepiness sign detection method is described. First, as shown in FIG. 2, linear accelerations and rotation angular velocities produced in the head are detected by the head movement detection unit 11 in Step S1. Here, in the case of installation in a vehicle such as an automobile, linear accelerations in a traveling direction, a vertical direction, and a lateral direction of a driver and rotation angular velocities in a rolling direction, a pitching direction, and a yawing direction of the driver are respectively detected and linear acceleration data and rotation angular velocity data are sent to the ideal eye movement angular velocity calculation unit 13. Although it is assumed here that the linear acceleration data in the vertical direction and the rotation angular velocity in the pitching direction are used, other components may also be used.

Next, in Step S2, the ideal eye movement angular velocity is calculated on the basis of the head movement detected in Step S1 by the ideal eye movement angular velocity calculation unit 13 and ideal eye movement angular velocity data is sent to the sleepiness sign detection unit 15.

In Step S3, eye movements are photographed to measure movement amounts of pupil center coordinates by the eye movement detection unit 12 and eye movement data in the respective rolling, pitching, and yawing directions of the driver is sent to the eye-rotation angular velocity calculation unit 14.

In Step S4, an eye-rotation angular velocity is calculated on the basis of the eye movement data obtained in Step S3 by the eye-rotation angular velocity calculation unit 14 and eye-rotation angular velocity data is sent to the sleepiness sign detection unit 15.

In Step S5, a VOR gain G and a residual standard deviation SDres shown below are calculated as the parameters on the vestibule-ocular reflex based on the ideal eye movement angular velocity data and the eye-rotation angular velocity data by the sleepiness sign detection unit 15. Here, the vestibule-ocular reflex (VOR) is a reflexive eye movement to obtain a clear vision by rotating eye balls substantially at the same velocity in an opposite direction to a head movement.

The VOR gain is calculated as a coefficient G of a regression model using an eye-rotation angular velocity e(t) as an objective variable and an ideal eye movement angular velocity h(t) and a constant term dc as explanatory variables by least squares estimation. Here, $\epsilon(t)$ is a residual of the regression model and $\tau$ is a delay time of an eye movement from an ideal eye movement. Here, the VOR gain may be calculated in at least one of the traveling direction, the vertical direction and the lateral direction of the driver.

$$e(t) = G \cdot h(t-\tau) + dc + \epsilon(t) \qquad \text{(Equation 1)}$$

The residual standard deviation SDres is calculated by the following equation. Here, N is the score of pieces of data to be measured.

$$SDres = \sqrt{\frac{1}{N-1} \sum_{t=1}^{N} \varepsilon^2(t)} \qquad \text{(Equation 2)}$$

Since a VOR gain decrease and a residual standard deviation increase occur before the driver becomes aware of sleepiness, they are effective as indices indicating a sign of sleepiness. Accordingly, in Step S6, the following indices are calculated by the sleepiness sign detection unit 15 to quantify a VOR gain increase and a residual standard deviation increase. In other words, since initial values and change amounts of the VOR gain and the residual standard deviation SDres differ between individuals, average values thereof in a highly arousal state are respectively calculated and change rates with respect to the average values are calculated. A VOR gain decrease rate $\Delta VOR(t)$ and an SDres increase rate $\Delta SDres(t)$ at a given time are defined and calculated as follows.

$$\Delta G(t) = -\frac{G(t) - \overline{G}}{\overline{G}} \times 100 \qquad \text{(Equation 3)}$$

$\overline{G}$: average value of VOR gain in highly arousal state $$\Delta SD(t) = -\frac{SDres(t) - \overline{SDres}}{\overline{SDres}} \times 100 \qquad \text{(Equation 4)}$$

$\overline{SDres}$: average value of residual standard deviation in highly arousal state In Step S7, the VOR gain decrease rate $\Delta VOR(t)$ and the SDres increase rate $\Delta SDres(t)$ calculated in Step S6 are respectively compared with threshold values th1, th2 set in advance by the sleepiness sign detection unit 15. If the VOR gain decrease rate $\Delta VOR(t)$ and the SDres increase rate $\Delta SDres(t)$ are both in excess of the threshold values (S7: YES), it is determined that a sleepiness sign has been detected and Step S8 follows. If at least one of the VOR gain decrease rate $\Delta VOR(t)$ and the SDres increase rate $\Delta SDres(t)$ is equal to or below the threshold value (S7: NO), it is determined that no sleepiness sign has been detected and a series of processings are finished.

In Step S8, a sleepiness sign detection signal is output by the sleepiness sign detection unit 15 and the series of processings are finished.

As described above, according to the sleepiness sign detection apparatus 10 of the present invention, a sign of sleepiness before a vehicle driver, a machine operator or the like becomes aware of sleepiness can be determined based on the vestibule-ocular reflex. Since the vestibule-ocular reflex is less subject to an external environment such as ambient brightness, an operating condition range can be widened. Further, since an operation load is small, real-time measurement and determination are possible.

In the above sleepiness sign detection method, processing orders of Steps S1 and S2 and Steps S3 and S4 are arbitrary.

EXAMPLE

Figure 3:
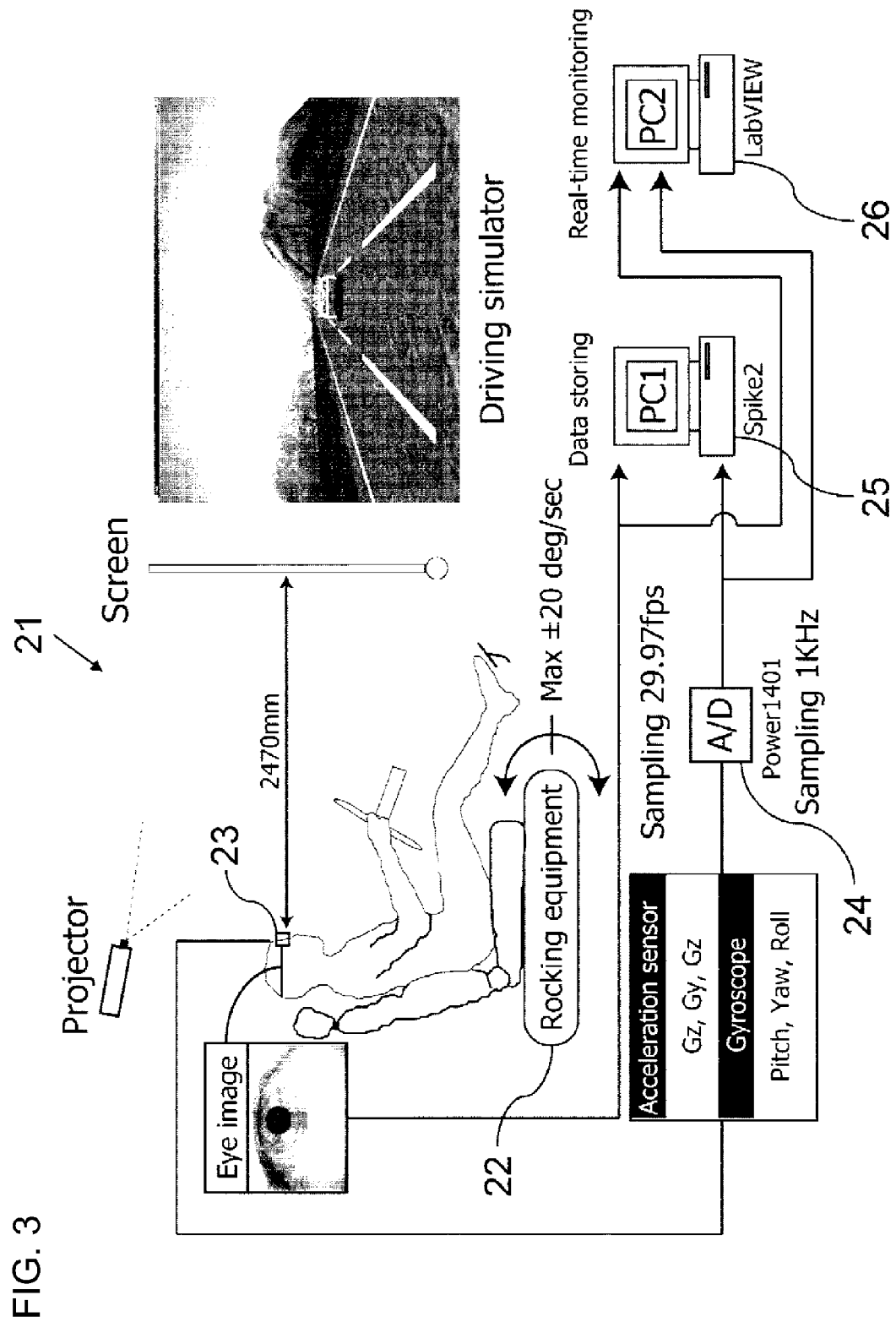
FIG. 3 is a schematic diagram of an experimental system simulating automobile driving.

An example of the present invention is shown below. FIG. 3 shows a schematic diagram of an experimental system simulating automobile driving. A driving simulator (DS) system 21 includes a projector and a screen for projecting DS images and a driver seat with a steering, an accelerator and a brake. The driver seat was installed at a position where the head of a subject and a center of the screen were right opposite to each other. A distance between the front surface of the head of the subject and the screen was 2470 mm, and a screen size was 10 inches (lateral view angle of ±39.1°, vertical view angle of ±26.3°). A vibrating device 22 for inducing vestibule-ocular reflex was installed below the driver seat. The luminance and contrast of the projector were so adjusted that a pupil diameter of the subject is substantially a median diameter (diameter of about 6 mm) of a pupil movable range.

Both eye images were measured at 29.97 fps by an eye movement scanner 23. Unillustrated three-axis acceleration sensor and three gyroscopes were mounted on the eye movement scanner 23 to measure linear accelerations and rotation angular velocities of the head movement respectively in three axis directions. The head movement data was synchronized with eye images, AD-converted by an AD/DA converter 24 at a sampling frequency of 1 kHz and stored in a data storage PC 25. Further, the eye images and the head movement data were branched and input to a processing PC 26 and the head movement, the eye movement and a pupil diameter change were observed in real time.

Here, the three-axis acceleration sensor and the gyroscopes correspond to the head movement detection unit, the eye movement scanner 23 corresponds to the eye movement detection unit and the processing PC 26 corresponds to the ideal eye movement angular velocity calculation unit, the eye-rotation angular velocity calculation unit and the sleepiness sign determination unit.

The subject sat on the driver seat in a natural posture after the eye movement scanner 23, the acceleration sensor and the gyroscopes were mounted and an experiment task described next was given to him.

In order to measure static eye positions, an instruction was given to fix a gaze point on an upper part of a number plate of a vehicle in front for 20 seconds after the start of a measurement in a state where the vibrating device 22 is not driven. Subsequently, the vibrating device 22 was driven to induce VOR after the elapse of 20 seconds. During this time, the subject performed a steering operation so as not to deviate from a driving lane while continuing to fix the gaze point. For 3 minutes after the driving device was driven, a simple mental arithmetic problem was given to maintain an arousal state. After the elapse of 3 minutes, an experimenter instructed to stop the mental arithmetic problem, but a DS operation and a vibratory stimulus were continued until an experiment was completed. A DS operation time was set at 15 minutes including a mental arithmetic problem period and, after the experiment, the subject was requested to make an introspective report on sleepiness during the mental arithmetic problem and during monotonous driving thereafter.

(Date Analysis) The ideal eye movement angular velocity $h(t)$ can be calculated from linear accelerations and rotation angular velocities produced in the head. Since contribution of linear accelerations was small in this example, calculation was made based on the rotation angular velocities of the head. The ideal eye movement angular velocity $h(t)$ was calculated by the processing PC 26 by being re-sampled at a sampling frequency of 29.97 Hz to match the number of pieces of data with that of pieces of the eye movement data after having noise removed by a digital band-pass filter. An eye movement angle and a pupil diameter were extracted and calculated through the calculation of the eye images obtained by the eye movement scanner 23 by the processing PC 26. The eye-rotation angular velocity $e(t)$ was calculated by differentiating the eye movement angle. Note that the ideal eye movement angular velocity $h(t)$ may also be calculated, taking into account linear accelerations produced in the head.

The VOR gain and the residual standard deviation (SDres) were calculated from the ideal eye movement angular velocity $h(t)$ and the eye-rotation angular velocity $e(t)$ by the processing PC 26. For the calculation of the VOR gain and the residual standard deviation (SDres), data for 40 seconds which gave sufficient estimation accuracy even after a fast phase was removed from the eye movement data was treated as 1 segment and a value in each segment was calculated every 10 seconds with subsequent segments overlapped for 30 seconds.

Figure 4A:
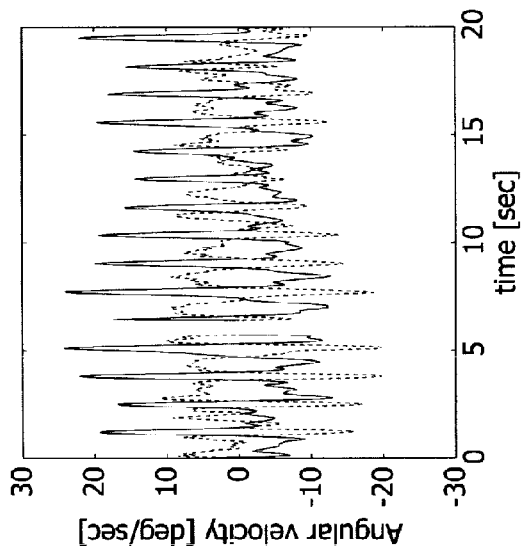
FIG. 4A is a plotting of ideal eye movement angular velocities and an eye-rotation angular velocities of typical subjects in an arousal state (while performing a mental arithmetic problem) in an overlapping manner.

(Test Results) FIG. 4A is a plotting of ideal eye movement angular velocities and eye-rotation angular velocities of typical subjects in an arousal state (during the mental arithmetic problem) in an overlapping manner. It can be confirmed that normal VOR, in which the eye movement is made substantially at the same velocity in a direction opposite to the head movement, is induced. FIG. 4B is a plotting of pieces of the data of FIG. 4A with a vertical axis representing the eye-rotation angular velocity and a horizontal axis representing the ideal eye movement angular velocity, where a straight line corresponds to a regression line of equation 1. In this example, the VOR gain was 0.802 and the SDres was 1.017.

Figure 4C:
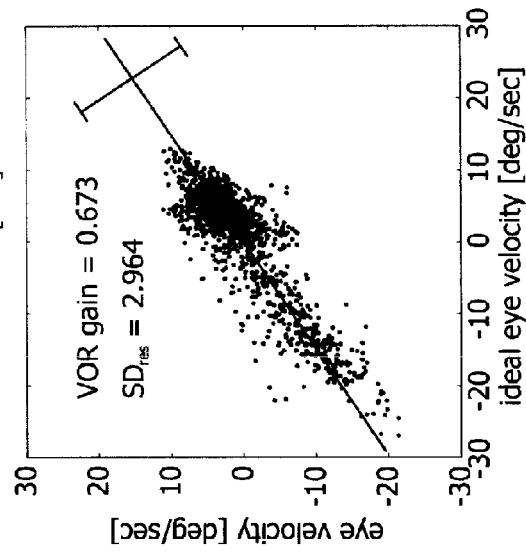
FIG. 4C shows test results in an interval in which the subjects felt sleepy, where FIG. 4C corresponds to FIG. 4A.
Figure 4B:
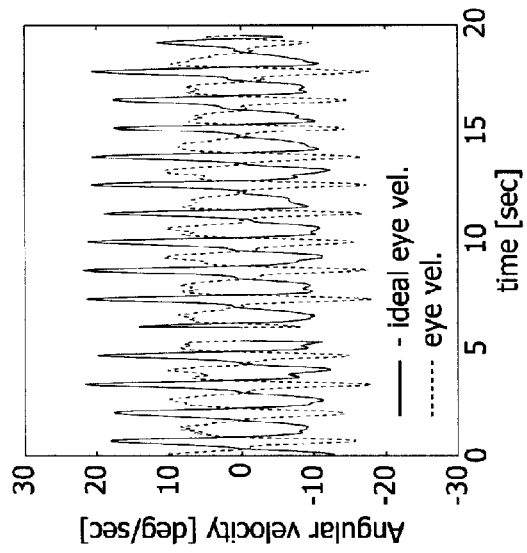
FIG. 4B is a plotting of data of FIG. 4A with a vertical axis representing the eye-rotation angular velocity and a horizontal axis representing the ideal eye movement angular velocity.
Figure 4D:
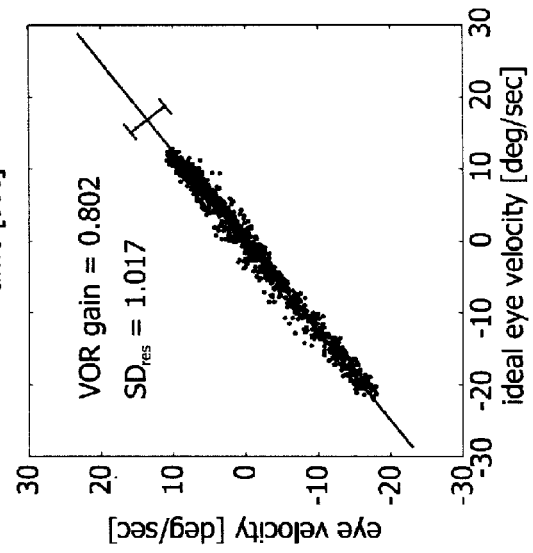
FIG. 4D shows test results in an interval in which the subjects felt sleepy, where FIG. 4D corresponding to FIG. 4B.

The test results in an interval in which the subjects felt sleepy are shown in FIGS. 4C and 4D. FIG. 4C corresponds to FIG. 4A and FIG. 4D corresponds to FIG. 4B. The VOR gain was 0.673 and the SDres was 2.964. The VOR gain decreased and the SDres increased as compared with those in the arousal state.

Figure 5:
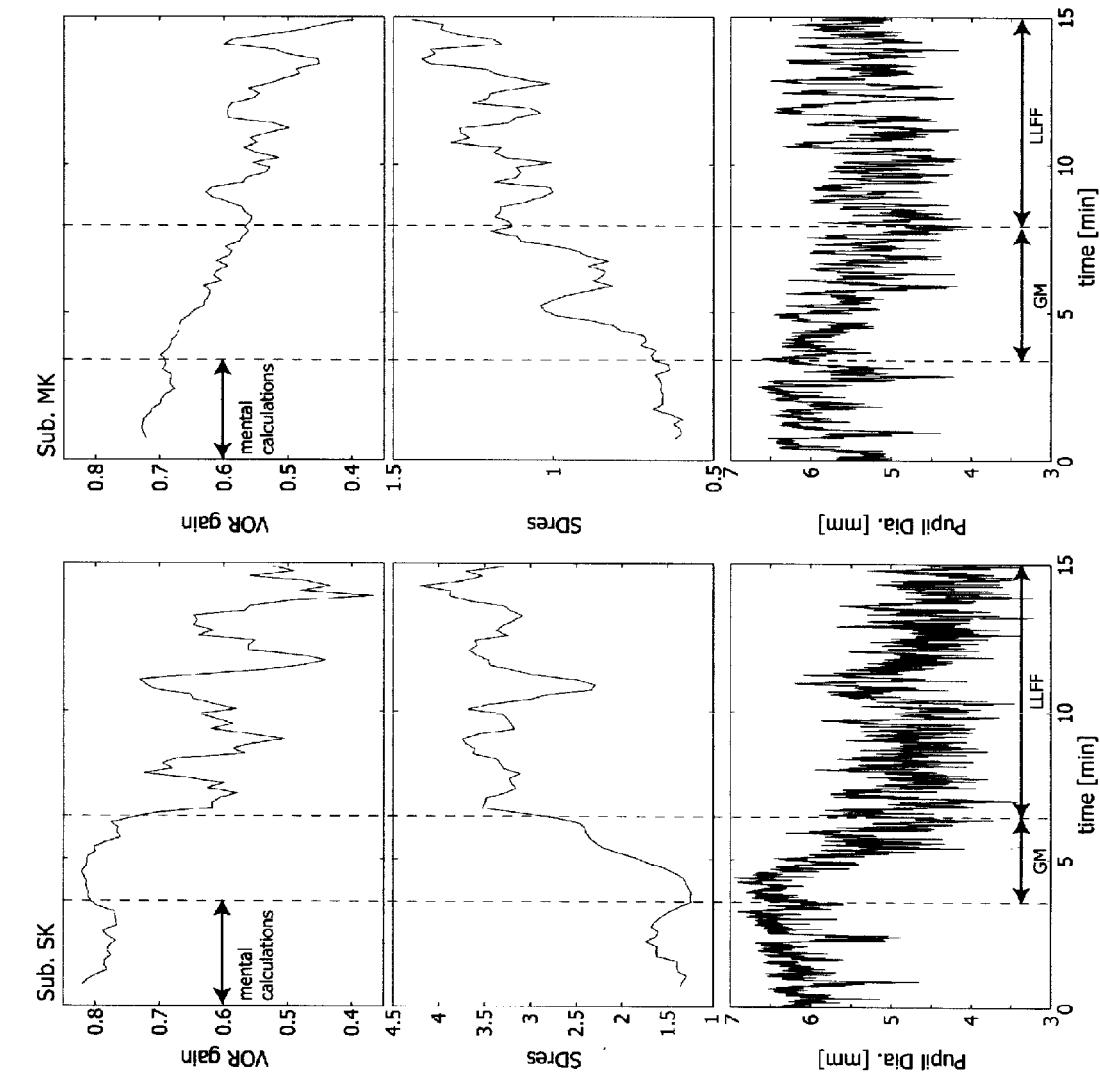
FIG. 5 is graphs comparing a VOR gain and an SDres with a pupil diameter change.

FIG. 5 is graphs showing comparisons of the VOR gain and the SDres with a pupil diameter change confirmed to be an effective sleepiness and its sign detection index. The VOR gain moderately decreases and, conversely, the SDres moderately increases for about 1 to 2 minutes after the stop of the mental arithmetic problem. Further, gradual miosis (GM) can be confirmed in the pupil diameter change in an interval in which the VOR gain and the SDres respectively decreases and increases. Studies made thus far indicate that the subject is not yet aware of sleepiness in this GM interval. In other words, characteristic changes, i.e. the VOR gain decrease and the SDres increase in this interval are sign signals of sleepiness.

After about 2 minutes following the start of gradual miosis, the VOR gain and the SDres respectively further decreases and increases and a large low frequency fluctuation (LLFF) can be confirmed in the pupil diameter. The LLFF is known to be a phenomenon which occurs while the subject perceives subjective sleepiness, and this coincides with the introspective report of the subject to the effect that he felt sleepy from a middle stage to the second half of the experiment. In other words, the VOR gain decrease and the SDres increase also serve as sign signals of sleepiness and indices of sleepiness.

Figure 6B:
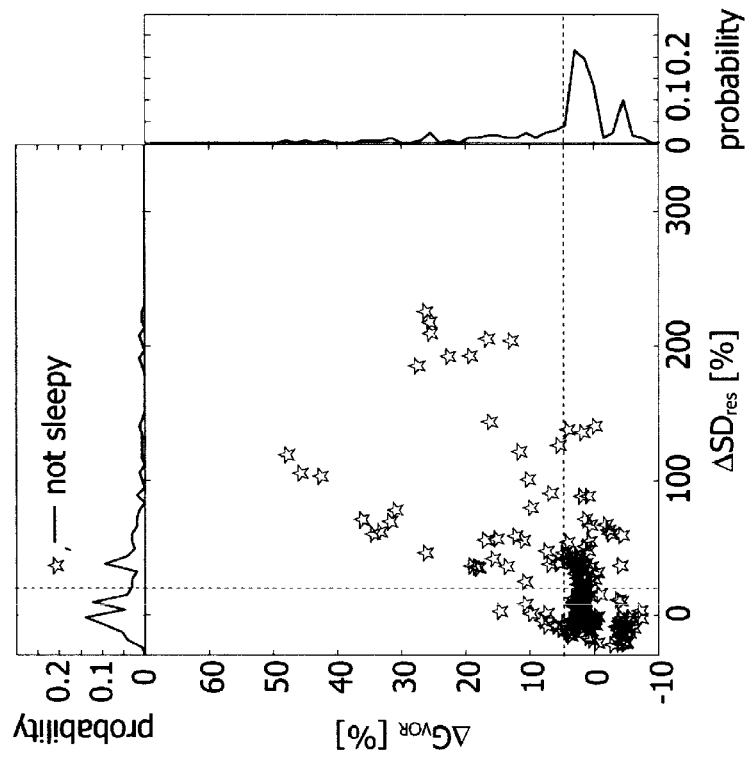
FIG. 6B is a plotting of $\Delta$VOR(t) and $\Delta$SDres(t) until the time when sleepiness is perceived after the time when a mental arithmetic program is finished.
Figure 6A:
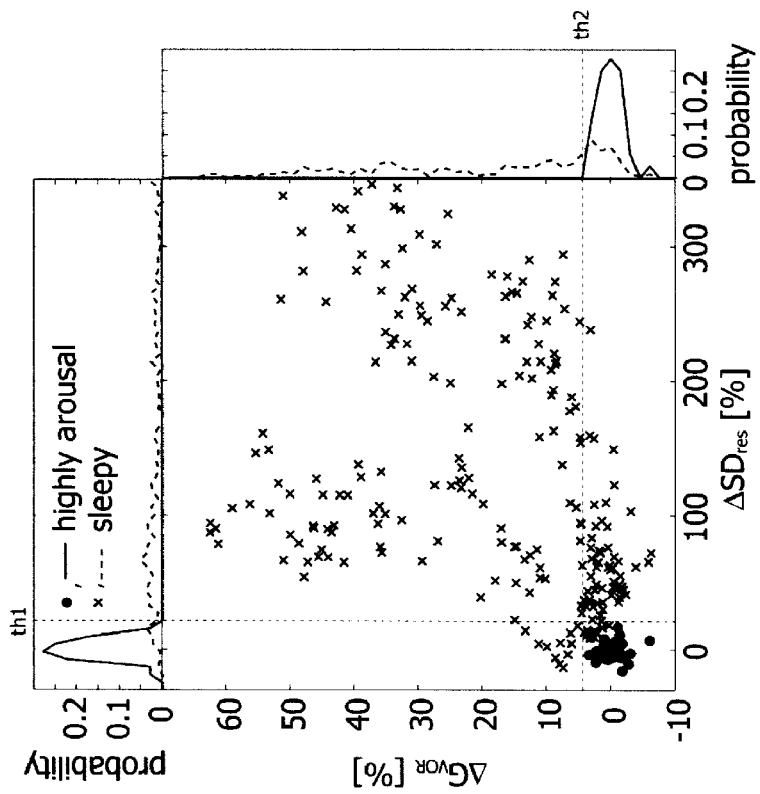
FIG. 6A is a plotting of VOR gain decrease rates $\Delta$VOR(t) and SDres increase rates $\Delta$SDres(t) at vertical and horizontal axes, respectively, for each of six pieces of experimental data.

(Sleepiness Sign Determination Method) In an experimental task with the same conditions as the above experiment, a subject was requested to make an introspective report on sleepiness every 2 minutes and a sign of sleepiness was determined from changes in the VOR gain and SDres. The VOR gain decrease rate ΔVOR(t) and the SDres increase rate ΔSDres(t) defined in equations 3 and 4 were used for determination. FIG. 6A is a plotting of the VOR gain decrease rates ΔVOR(t) and the SDres increase rates ΔSDres(t) in six pieces of experimental data with a vertical axis representing the VOR gain decrease rate ΔVOR(t) and a horizontal axis representing the SDres increase rate ΔSDres(t). Mark "•" indicates an arousal state and mark "x" indicates data in the interval in which sleepiness was felt. In an upper part and a right part of FIG. 6A, distributions of the respective states were plotted while being so weighted that the entire area became 1. Here, threshold values were set for ΔVOR(t) and ΔSDres(t) so as to include all pieces of data in the arousal state, and areas below the two threshold values were set as arousal areas and those above the threshold values were set as sleepiness area. FIG. 6B is a plotting of ΔVOR(t) and ΔSDres(t) until sleepiness was perceived after the end of the mental arithmetic problem. 95% pieces of the data reported to have perceived sleepiness in FIG. 6A are plotted in the sleepiness area, and separation of a sleepy state and a non-sleepy state can be confirmed. As can be understood from the respective distributions shown in FIG. 6B, most pieces of data are present in the arousal area, whereas some pieces of the data are preset in the sleepiness area.

Here, a state where sleepiness was not perceived, which state was plotted in the sleepiness area and continued for 40 seconds or more, was defined as a sign signal of sleepiness. This is because there is a possibility of including the influence of the overlap when this state continues for 30 seconds or less. As a result, a sign of sleepiness was confirmed for 5 pieces of data (83.3%). The one piece of data in which no sign of sleepiness was confirmed was also plotted in the sleepiness area, but was not confirmed as a sign of sleepiness since the state did not continue for 40 seconds or more.

By setting subject-independent threshold values for the highly arousal states of the respective subjects defined in advance in this way, it was confirmed that a sign of sleepiness could be easily detected for most of the subjects.

(Advantageous Effects of Specific Embodiments) (1) According to the sleepiness sign detection apparatus 10 of the present invention, it is possible to detect the head movement by the head movement detection unit 11, detect the eye movement by the eye movement detection unit 12, calculate the ideal eye movement angular velocity based on the head movement data detected by the head movement detection unit 11 by the ideal eye movement angular velocity calculation unit 13, calculate the eye-rotation angular velocity based on the eye movement data detected by the eye movement detection unit 12 by the eye-rotation angular velocity calculation unit 14 and detect the vestibule-ocular reflex (VOR) from the ideal eye movement angular velocity and the eye-rotation angular velocity and determine a sign of sleepiness before a vehicle driver, a machine operator or the like perceives sleepiness based on this vestibule-ocular reflex by the sleepiness sign determination unit. Since the vestibule-ocular reflect is less subject to an external environment such as ambient brightness, an operating condition range can be widened. Further, since an operation load is small, real-time measurement and determination are possible.

(2) Since the VOR gain decrease and the residual standard deviation increase occur before sleepiness is perceived, they are effective indices indicating a sign of sleepiness. The VOR gain decrease rate ΔVOR(t) and the SDres increase rate ΔSDres(t) are respectively calculated and compared with the threshold values th1, th2 set in advance by the sleepiness sign detection unit 15, and detection of a sign of sleepiness can be determined when both the VOR gain decrease rate ΔVOR(t) and the SDres increase rate ΔSDres(t) exceed the threshold values. Thus, it was confirmed that a sign of sleepiness can be easily detected for most subjects.

(3) In the case of using the sleepiness sign detection apparatus by installing it in a vehicle, the ideal eye movement angular velocity can be calculated using outputs of an acceleration sensor and a gyro sensor provided in the vehicle as the head movement detection unit. Thus, the number of constituent elements of the sleepiness sign detection apparatus can be reduced.

(Other Embodiments) (1) Although it is judged whether both the VOR gain decrease rate ΔVOR(t) and the SDres increase rate ΔSDres(t) are in excess of the threshold values in Step S7, only either one of them may be calculated and a sign of sleepiness may be determined based on whether or not the calculated value is in excess of the threshold value as a simple measure.

(2) The sleepiness sign detection signal output in Step S8 may be input to a warning device, which may, in turn, vibrate the seat, fasten a seat belt, give an audible warning or employ another method to arouse a driver.

(3) Although the three-axis acceleration sensor and the gyroscopes are used as the head movement detection unit 11, the head movement detection unit 11 is not limited to these provided that it can detect the head movement. For example, face images of a driver or an operator may be taken, and analyzed in the eye-rotation angular velocity calculation unit 14 to detect a facing direction of each frame, thereby detecting a head movement. In this case, the head movement detection unit 11 may double as a CCD camera used as the eye movement detection unit 12.

The above embodiments of the present invention are simply for facilitating the understanding of the present invention and are not in any way to be construed as limiting the present invention. The present invention may variously be changed or altered without departing from its spirit and encompass equivalents thereof.

What is claimed is:

1. A sleepiness sign detection apparatus, comprising:
a head movement detection unit configured to detect a head movement to generate a head movement data;
an eye movement detection unit configured to detect an eye movement to generate an eye movement data;
an ideal eye movement angular velocity calculation unit configured to calculate an ideal eye movement angular velocity based on the head movement data generated by the head movement detection unit;
an eye-rotation angular velocity calculation unit configured to calculate an eye-rotation angular velocity based on the eye movement data generated by the eye movement detection unit; and
a sleepiness sign detection unit configured to detect vestibule-ocular reflex (VOR) from the ideal eye movement angular velocity and the eye-rotation angular velocity, and determine a sign of sleepiness based on the vestibule-ocular reflex.

2. The sleepiness sign detection apparatus according to claim 1, wherein
the sleepiness sign detection unit calculates a VOR gain defined by G and a decrease rate of the VOR gain, the G obtained by approximating the eye-rotation angular velocity by a linear equation of the ideal eye movement angular velocity:

$$e(t)=G \cdot h(t-\tau)+dc+\epsilon(t),$$

where e(t) represents eye-rotation angular velocity; G represents VOR gain; h(t) represents ideal eye movement angular velocity; τ represents delay time of eye movement with respect to head movement; dc represents constant term; and ϵ(t) represents residual of regression model, and determines a sign of sleepiness, when the decrease rate of the VOR gain exceeds a threshold value set in advance.

3. The sleepiness sign detection apparatus according to claim 1, wherein the sleepiness sign detection unit calculates an approximation residual defined by ϵ(t) and a residual standard deviation, the ϵ(t) obtained by approximating the eye-rotation angular velocity by a linear equation of the ideal eye movement angular velocity:

$$e(t)=G \cdot h(t-\tau)+dc+\epsilon(t),$$

where e(t) represents eye-rotation angular velocity; G represents VOR gain; h(t) represents ideal eye movement angular velocity; τ represents delay time of eye movement with respect to head movement; dc represents constant term; and ϵ(t) represents residual of regression model, and determines a sign of sleepiness, when an increase rate of the residual standard deviation exceeds a threshold value set in advance.

4. The sleepiness sign detection apparatus according to claim 2, wherein the sleepiness sign detection unit calculates an approximation residual defined by ϵ(t) and a residual standard deviation, the ϵ(t) obtained by approximating the eye-rotation angular velocity by a linear equation of the ideal eye movement angular velocity:

$$e(t)=G \cdot h(t-\tau)+dc+\epsilon(t),$$

where e(t) represents eye-rotation angular velocity; G represents VOR gain; h(t) represents ideal eye movement angular velocity; τ represents delay time of eye movement with respect to head movement; dc represents constant term; and ϵ(t) represents residual of regression model, and determines a sign of sleepiness, when an increase rate of the residual standard deviation exceeds a threshold value set in advance.

5. The sleepiness sign detection apparatus according to claim 1, wherein the sleepiness sign detection apparatus is a sleepiness detection apparatus installed in a vehicle, and the ideal eye movement angular velocity is calculated on the basis of outputs of an acceleration sensor and a gyro sensor provided in the vehicle as the head movement detection unit.

6. The sleepiness sign detection apparatus according to claim 2, wherein the sleepiness sign detection apparatus is a sleepiness detection apparatus installed in a vehicle, and the ideal eye movement angular velocity is calculated on the basis of outputs of an acceleration sensor and a gyro sensor provided in the vehicle as the head movement detection unit.

7. The sleepiness sign detection apparatus according to claim 3, wherein the sleepiness sign detection apparatus is a sleepiness detection apparatus installed in a vehicle, and the ideal eye movement angular velocity is calculated on the basis of outputs of an acceleration sensor and a gyro sensor provided in the vehicle as the head movement detection unit.

8. The sleepiness sign detection apparatus according to claim 4, wherein the sleepiness sign detection apparatus is a sleepiness detection apparatus installed in a vehicle, and the ideal eye movement angular velocity is calculated on the basis of outputs of an acceleration sensor and a gyro sensor provided in the vehicle as the head movement detection unit.

* * * * *